(12) United States Patent
Owens et al.

(10) Patent No.: US 10,451,602 B2
(45) Date of Patent: Oct. 22, 2019

(54) COMPOSITION AND METHOD OF SCREENING HYDROCARBONS TO LIMIT POTENTIAL TOXICOLOGICAL HAZARDS

(71) Applicant: ExxonMobil Research and Engineering Company, Annandale, NJ (US)

(72) Inventors: Tracie L. Owens, Houston, TX (US); Beatrice M. Gooding, Hopewell, NJ (US); Frank C. Wang, Annandale, NJ (US); Yogi V. Shukla, Cherry Hill, NJ (US); Eugenio Sanchez, Pitman, NJ (US); Charles L. Baker, Jr., Thornton, PA (US); Roland B. Saeger, Runnemede, NJ (US)

(73) Assignee: ExxonMobil Research And Engineering Company, Annandale, NJ (US)

( * ) Notice: Subject to any disclaimer, the term of this patent is extended or adjusted under 35 U.S.C. 154(b) by 174 days.

(21) Appl. No.: 15/471,476

(22) Filed: Mar. 28, 2017

(65) Prior Publication Data
US 2017/0284995 A1 Oct. 5, 2017

Related U.S. Application Data

(60) Provisional application No. 62/315,944, filed on Mar. 31, 2016.

(51) Int. Cl.
*G01N 33/28* (2006.01)
*C10M 101/02* (2006.01)
(Continued)

(52) U.S. Cl.
CPC ......... *G01N 33/2835* (2013.01); *B01D 53/30* (2013.01); *C10M 101/02* (2013.01);
(Continued)

(58) Field of Classification Search
CPC ..................................................... G01N 33/28
See application file for complete search history.

(56) References Cited

U.S. PATENT DOCUMENTS

| | | | |
|---|---|---|---|
| 4,499,187 A | 2/1985 | Blackburn et al. | |
| 5,034,119 A | 7/1991 | Blackburn et al. | |

(Continued)

FOREIGN PATENT DOCUMENTS

| | | |
|---|---|---|
| WO | 2011110551 A1 | 9/2011 |
| WO | 2014037481 A1 | 3/2014 |
| WO | 2015077769 A1 | 5/2015 |

OTHER PUBLICATIONS

McKee et al, "Genetic Toxicity of High-Boiling Petroleum Substances", Regulatory Toxicology and Pharmacology, Mar. 14, 2013, pp. S75-S85, vol. 67, No. 2, Elsevier Inc.
(Continued)

*Primary Examiner* — Ellen M McAvoy
(74) *Attorney, Agent, or Firm* — Robert A. Migliorini; Scott F. Yarnell (57) ABSTRACT

A method of screening a hydrocarbon stream for potential toxicological hazards. The method involves providing a hydrocarbon stream; conducting 2-dimensional gas chromatography (2D-GC) analysis to quantify saturates and aromatic distribution in the hydrocarbon stream; identifying 2-8 ring aromatic distribution and weight percentage of 2-8 ring aromatic molecules in the hydrocarbon stream from the 2D-GC analysis; relating the weight percentage of 2-8 ring aromatic molecules in the hydrocarbon stream from the 2D-GC analysis to a mutagenicity index (MI), in which the MI is determined in accordance with ASTM Standard Method E 1687; and assessing a potential toxicological hazard of the hydrocarbon stream based on the weight percentage of 2-8 ring aromatic molecules in the hydrocarbon stream from the 2D-GC analysis and a MI threshold
(Continued)

value. The 2-8 ring aromatic distribution preferably includes 3-6 ring aromatics, more preferably 3.5-5.5 ring aromatics. The 2-8 ring aromatic distribution includes mono alkylated and multi alkylated aromatic molecules.

31 Claims, 11 Drawing Sheets

(51) Int. Cl.
*G01N 30/88* (2006.01)
*B01D 53/30* (2006.01)
*G01N 30/02* (2006.01)
*G01N 30/46* (2006.01)

(52) U.S. Cl.
CPC ..... *G01N 30/88* (2013.01); *C10G 2300/1048* (2013.01); *C10G 2300/1062* (2013.01); *C10M 2203/003* (2013.01); *G01N 30/463* (2013.01); *G01N 2030/025* (2013.01); *G01N 2030/8854* (2013.01)

(56) References Cited

U.S. PATENT DOCUMENTS

| | | | | |
|---|---|---|---|---|
| 6,146,520 | A * | 11/2000 | Gupte | C10G 21/02 208/311 |
| 8,682,597 | B2 | 3/2014 | Brown et al. | |
| 2008/0163672 | A1 * | 7/2008 | Wang | C10G 67/04 73/23.39 |
| 2014/0262958 | A1 * | 9/2014 | Sircar | G01N 33/2823 208/309 |
| 2015/0107331 | A1 * | 4/2015 | Wang | G01N 30/72 73/23.37 |
| 2015/0218464 | A1 * | 8/2015 | Schleicher | C10G 65/02 585/253 |
| 2016/0187253 | A1 * | 6/2016 | Koseoglu | G01N 21/33 702/30 |
| 2016/0195481 | A1 * | 7/2016 | Koseoglu | G01N 33/24 374/14 |
| 2016/0313237 | A1 * | 10/2016 | Young | G01N 21/31 |
| 2016/0363533 | A1 * | 12/2016 | Koseoglu | G01N 21/64 |
| 2017/0370830 | A1 * | 12/2017 | Koseoglu | G01N 33/2823 |
| 2018/0017500 | A1 * | 1/2018 | Pelletier | G01N 21/3504 |
| 2018/0050282 | A1 * | 2/2018 | Nagai | B01D 15/08 |

OTHER PUBLICATIONS

The International Search Report and Written Opinion of PCT/US2017/024676 dated Sep. 19, 2017.

Mackerer, Carl R., et al., Petroleum Mineral Oil Refining and Evaluation of Cancer Hazard, Applied Occupational and Environmental Hygiene, 18:11, 2003, Taylor & Francis, Oxford, NY.

Chasey, K.L., et al., Evaluation of the Dermal Carcinogenicity of Lubricant Base Oils by the Mouse Skin Painting Bioassay and Other Proposed Methods, Journal of Applied Toxicology, vol. 13(1), 1993, John Wiley & Sons, Ltd., Hoboken, NJ.

* cited by examiner

| Sample Number | Sample Description | 700°F-800°F | | | | 800°F-900°F | | | | | MI |
|---|---|---|---|---|---|---|---|---|---|---|---|
| | | 3.5-Ring-ARO | 4.0-Ring-ARO | 5.0-Ring-ARO | 5.5-Ring-ARO | 3.5-Ring-ARO | 4.0-Ring-ARO | 4.5-Ring-ARO | 5.0-Ring-ARO | 5.5-Ring-ARO | |
| 15-106926 | Catalytic base oil | 1,448 | 215 | 44 | 0 | 7,834 | 2,073 | 809 | 793 | 292 | 0.82 |
| 15-107696 | Catalytic base oil | 4,241 | 1,913 | 783 | 53 | 11,832 | 5,955 | 4,730 | 6,451 | 2,090 | 0.97 |
| 15-78783 | Catalytic base oil | 1,085 | 1 | - | - | 5,108 | 717 | 29 | 8 | - | 0 |
| 15-80972 | Catalytic base oil | 710 | 135 | 31 | 1 | 3,737 | 488 | 222 | 195 | 13 | 0.2 |
| 15-93588 | Catalytic base oil | 1,070 | 141 | 17 | - | 6,897 | 1,231 | 488 | 359 | 16 | 0 |
| 01-058031 | raffinate | 2,403 | 18 | - | - | 20,910 | 1,209 | 1 | - | - | 0 |
| 01-058032 | raffinate | 2,452 | 21 | - | - | 22,423 | 1,546 | 11 | - | - | 0.2 |
| 01-058033 | raffinate | 3,786 | 26 | - | - | 28,504 | 2,723 | 57 | - | - | 0.1 |
| 01-058724 | Group I base oil | 25,204 | 5,298 | 691 | 0 | 54,617 | 19,367 | 11,220 | 2,923 | - | 1.6 |
| 01-060457 | Light distillate | 3,781 | 308 | - | - | 7 | - | - | - | - | 0.8 |
| 01-061614 | Light distillate | 127 | 104 | 48 | - | - | 1 | 0 | 1 | - | 0.4 |
| 01-58725 | raffinate | 8,814 | 1,127 | 11 | - | 29,003 | 8,577 | 2,377 | 239 | - | 0.3 |
| 02-001458 | Light distillate | 21,887 | 1,730 | 58 | - | - | - | - | - | - | 1.7 |
| 02-009054 | Heavy distillate | 1,919 | 149 | - | - | - | - | - | - | - | 0.5 |
| 02-030765 | Heavy distillate | 32,017 | 9,121 | 1,605 | 3 | 41,445 | 23,963 | 15,988 | 7,829 | 91 | 5.1 |
| 03-017911 | Light distillate | 12,061 | 533 | 5 | - | - | - | - | - | - | 0.5 |
| 03-022831 | Hydrocracker bottoms | 296 | 307 | 178 | 0 | 1,414 | 7 | 72 | 434 | 24 | 1.4 |
| 03-031229 | Heavy distillate (VGO) | 48,516 | 17,617 | 3,043 | 86 | 46,048 | 29,305 | 23,132 | 14,470 | 266 | 7.3 |
| 97-014945 | Heavy distillate (VGO) | 70,945 | 24,420 | 5,296 | 10 | 17,385 | 12,718 | 11,638 | 2,050 | 0 | 6.4 |
| 98-040147 | Raffinate | 30,031 | 6,231 | 707 | - | 13,034 | 5,578 | 2,476 | 73 | - | 2.4 |
| 01-054838 | Heavy distillate (VGO) | 2,487 | 600 | 7 | 2 | 1 | 0 | - | 1 | 1 | 0.9 |
| 13-061950 | Catalytic base oil | 421 | - | - | - | 7,123 | 606 | - | - | - | 0.02 |
| 13-100974 | Group I base oil | 367 | - | - | - | 10,473 | 1,842 | 1 | - | - | 0 |
| 13-042773 | Heavy distillate | 7,748 | 3,884 | 567 | - | 12,463 | 7,367 | 2,731 | 499 | 13 | 2.14 |
| 02-002341 | Raffinate | 5,381 | 785 | 1 | - | 9,337 | 4,243 | 33 | - | - | 0.3 |
| 13-092960 | Heavy distillate | 28,810 | 12,809 | 1,187 | - | 35,986 | 37,594 | 16,746 | 1,344 | 1 | 3.9 |
| 02-002329 | Extract | 101,628 | 62,413 | 10,106 | 1 | 65,717 | 100,368 | 79,265 | 10,747 | 326 | 17.86 |
| 02-002344 | Heavy raffinate | 1 | - | - | - | 15,080 | 7,273 | 1,915 | 2 | - | 0.5 |

Fig 11
Functional form for computing MI from compositions

COMPOSITION AND METHOD OF SCREENING HYDROCARBONS TO LIMIT POTENTIAL TOXICOLOGICAL HAZARDS

CROSS-REFERENCE TO RELATED APPLICATIONS

This application claims priority to U.S. Provisional Application No. 62/315,944 filed Mar. 31, 2016, which is herein incorporated by reference in its entirety.

FIELD

This disclosure provides a preferred composition and a method of screening a hydrocarbon stream for potential toxicological hazards by relating the amount of 2-8 ring aromatics in the hydrocarbon stream, as determined by 2-dimensional gas chromatography (2D-GC) analysis, to a mutagenicity index (MI). The method is field deployable, providing real time feedback during operations.

BACKGROUND

Feed flexibility at lube refineries is managed to minimize risk of producing lube base stock outside of fit for purpose product quality standards. Crude approval procedures have long been established based on predictions of the ability of a crude to meet oxidative stability and fit for purpose standards.

Assessment of toxicological hazards is based on processing experience and measurement of a MI of processed base oils. However, obtaining the MI measurement takes a few weeks and it cannot be measured on all plant batches although good practice dictates that it should be checked during routine quality monitoring or as part of significant feed or process changes.

A compositional model based on multi-ring aromatics in base oils can be used for estimation of toxicological hazards. Also, conservative ultraviolet absorption spectra of aromatic hydrocarbons (UV aromatics) and viscosity index (VI) thresholds are set for the purpose of monitoring potential toxicological hazards of base oils. Other techniques, such as High Detail Hydrocarbon Analysis (HDHA) can also be suitable.

The development of a screening method is needed that can estimate toxicological potential of hydrocarbons. Also, the development of a screening method is needed that will reduce the barriers to entry of demonstrations (e.g., cost, time, human resources, tied-up tankage, etc.), reduce the number of demonstrations needed, allow for more effective capture of feed flexibility credits, and reduce product giveaway during Group I/II/III/III+ base stock production at refineries.

SUMMARY

In accordance with this disclosure, assessment of potential toxicological hazards of a hydrocarbon mixture can be made by measuring MI of processed base oils. The MI threshold value for such a single point assessment is preferably 0.4. Base oils for which the MI is greater than 0.4 are candidates to be more fully analyzed for their potential health hazards. 2D-GC quantification of 2-8 ring aromatics exhibits a stronger relationship with MI than other quick methods to quantify the level of multi-ring aromatics in samples, such as UV aromatics and VI. It has been found, in accordance with this disclosure, that evaluation with 2D-GC of a diverse set of samples (i.e., crude, distillate, raffinate, extract, and dewaxed oil) originating from various hydrocarbon streams showed the 3.5-5.5 aromatic ring class region of 2D-GC spectra were present in samples with MI greater than 0.4, yet missing from samples with MI less than 0.4. The 2D-GC analysis can quantify multi-ring aromatics in a similar fashion to High definition hydrocarbon analysis (HDHA), and the 2D-GC method is faster and less expensive.

This disclosure relates in part to a method of screening a hydrocarbon stream for potential toxicological hazards. The method involves providing a hydrocarbon stream; conducting 2D-GC analysis to quantify saturates and aromatic distribution in the hydrocarbon stream; identifying 2-8 ring aromatic distribution and weight percentage of 2-8 ring aromatic molecules in the hydrocarbon stream from the 2D-GC analysis; relating the weight percentage of 2-8 ring aromatic molecules in the hydrocarbon stream from the 2D-GC analysis to a MI, in which the MI is determined in accordance with ASTM Standard Method E 1687; and assessing a potential toxicological hazard of the hydrocarbon stream based on the weight percentage of 2-8 ring aromatic molecules in the hydrocarbon stream from the 2D-GC analysis and a MI threshold value. The 2-8 ring aromatic distribution preferably comprises 3-6 ring aromatics, more preferably 3.5-5.5 ring aromatics. The 2-8 ring aromatic distribution comprises mono alkylated and multi alkylated aromatic molecules.

This disclosure also relates in part to a method of characterizing a hydrocarbon stream. The method involves providing a hydrocarbon stream; conducting 2D-GC analysis to quantify saturates and aromatic distribution in the hydrocarbon stream; identifying 2-8 ring aromatic distribution and weight percentage of 2-8 ring aromatic molecules in the hydrocarbon stream from the 2D-GC analysis; and relating the weight percentage of 2-8 ring aromatic molecules in the hydrocarbon stream from the 2D-GC analysis to a MI, in which the MI is determined in accordance with ASTM Standard Method E 1687. In a preferred embodiment, the method further involves assessing a potential toxicological hazard of the hydrocarbon stream based on the weight percentage of 2-8 ring aromatic molecules in the hydrocarbon stream from the 2D-GC analysis and a MI threshold value. The 2-8 ring aromatic distribution preferably comprises 3-6 ring aromatics, more preferably 3.5-5.5 ring aromatics. The 2-8 ring aromatic distribution comprises mono alkylated and multi alkylated aromatic molecules. In this nomenclature, fractional ring aromatics are generally ascribed to molecules with saturated ring structure within the molecule, such as naphthene-aromatics.

In accordance with this disclosure, the robustness or strength of the relationship between MI and the weight percentage of 2-8 ring aromatic molecules, preferably 3-6 ring aromatic molecules, more preferably 3.5-5.5 ring aromatic molecules, identified by completing 2D-GC analysis in the hydrocarbon stream is greater or improved as compared to the robustness or strength of the relationship between MI and the weight percentage of 2-8 ring aromatic molecules, preferably 3-6 ring aromatic molecules, more preferably 3.5-5.5 ring aromatic molecules, identified by completing UV aromatics or related analysis in the hydrocarbon stream. For example, MI is known to vary with molecular weight, therefore process streams originating from different refinery units or distillation fractions can have similar aromatic distributions but vastly different MI. Due to the ability of 2D-GC to determine the boiling point distribution of saturates and aromatics, the relationship between 2D-GC aromatics and MI of the hydrocarbon stream will better capture the impact of hydrocarbon molecular weight on potential toxicological hazards than UV aromatics or related analysis, which do not quantify molecular weight distribution of hydrocarbon streams.

The method of this disclosure enables a lube refinery to more effectively capture feed flexibility credits and reduce product give away during Group I/II/III/III+ base stock production.

2D-GC is a faster and less expensive method to identify multi-ring aromatics than more detailed techniques, and 2D-GC can identify a broader range of aromatic classes than other quick methods. It has the potential to be field deployable, providing real time feedback during commercial feed selection and stock switching at refineries.

This disclosure further relates in part to a composition comprising a middle distillate boiling range refined petroleum stream having a 4.5 ring value of less than about 0.10, a final boiling point (FBP) of less than about 960° F., and a MI of 1. In particular, the composition has a kinematic viscosity at 100° C. between about 4 and about 6 cSt, and a viscosity index (VI) of at least 75. Preferably, the distillate is a refined lube base stock suitable for formulation in lubricants.

Other objects and advantages of the present disclosure will become apparent from the detailed description that follows.

Alternate methods can also be employed that have analytical discrimination around the various aromatics ring classes. While requiring longer time and higher levels of effort, detailed composition can be estimated as described in U.S. Pat. No. 8,682,597, herein incorporated by reference, which is often referred to as high detail hydrocarbon analysis (HDHA).

BRIEF DESCRIPTION OF THE DRAWINGS

FIG. 6 shows data summarized from the graphs of FIGS. 2 to 5 in accordance with Example 3.

DETAILED DESCRIPTION

All numerical values within the detailed description and the claims herein are modified by "about" or "approximately" the indicated value, and take into account experimental error and variations that would be expected by a person having ordinary skill in the art.

In accordance with this disclosure, petroleum or other hydrocarbon samples are analyzed by 2D-GC. The petroleum/hydrocarbon samples can be, for example, one or more samples from a whole crude, a total liquid product (TLP) from a process unit, a total liquid product from a research or refinery process development, a fraction, distillate or intermediate stream of whole crude, TLP or intermediate, or a fraction, distillate or intermediate stream from a research or refinery process.

2D-GC separates petroleum molecules into various compound classes. In the 2D-GC methods described herein, the first dimension separated petroleum molecules can be, for example, by boiling point (primarily influenced by carbon number). The second dimension of GC separated petroleum molecules can be, for example, by polarity (primarily influenced by aromaticity or aromatic groups). The 2D-GC compound classes include, for example, paraffins, 1-ring naphthenes, 2-ring+naphthenes, 1-ring aromatics, 1-ring naphthenic aromatics (1.5-ring aromatics), 2-ring aromatics, 2-ring naphthenic aromatics (2.5-ring aromatics), 3-ring aromatics, 3-ring naphthenic aromatics (3.5-ring aromatics), 4-ring aromatics, 4-ring naphthenic aromatics (4.5-ring aromatics) 5-ring+aromatics, 5-ring naphthenic aromatics (5.5-ring aromatics), and the like. 2D-GC also allows for determination of total normal paraffin concentrations and carbon number distributions. By analyzing a reference (a material that can completely elute from a 2D-GC system, such as diesel), a recovery or yield can be determined for the analyte samples. Additionally, the boiling range may be determined. A convenient method for specifying boiling range would be the end points of the range or the average. For example, a 750 cut is specified to have and median booing point of 750 deg F. and could be also specified as the material boiling substantially between 700 and 800 deg F. by 2DGC.

In this disclosure, reference may be made to hydrocarbon streams, hydrocarbon samples, and/or hydrocarbon mixtures. Hydrocarbon streams, samples, or mixtures are defined herein to include streams, samples, or mixtures containing aromatics. As understood by those of skill in the art, a typical mineral petroleum feedstock often includes compounds containing, for example, one-ring naphthenes, two-ring naphthenes, other multi-ring naphthenes, 1-ring aromatics, two-ring aromatics, other multi-ring aromatics, 1-ring naphthenic aromatics, 2-ring naphthenic aromatics, other multi-ring naphthenic aromatics, and the like. Unless it is specifically indicated otherwise, hydrocarbon streams, samples, or mixtures are defined to include streams, samples, or mixtures containing compounds that include such aromatics.

In this disclosure, reference will be made to screening petroleum samples and/or hydrocarbon samples. A petroleum and/or hydrocarbon sample can be obtained in any convenient manner. An initial source for a sample can correspond to a raw or virgin mineral feed, a non-conventional feed such as a synthetic crude or a biologically derived oil, an output from a refinery process, or a combination of any of the above. When performing the analysis described herein, a single sample of a desired hydrocarbon for study can be obtained and then divided into multiple portions for analysis. Alternatively, multiple samples can be separately obtained from the initial hydrocarbon source. Still another option is to use any other convenient technique for providing samples to the analysis techniques. Of course, an "initial hydrocarbon source" can also be created by mixing portions from a plurality of hydrocarbon sources to create samples (or a source for samples).

In 2D-GC, a pair of chromatography columns is used in order to perform a more thorough separation. For example, a first column can provide a separation based on boiling point (primarily influenced by carbon number) while a second column provides separation based on aromaticity or aromatic groups. During operation, the second column preferably performs a relatively fast separation as compared with the first column, in order to reduce or minimize any overlap between species that were effectively separated in the first column.

As noted above, the first separation stage can correspond to a GC separation stage based on, for example, boiling point (primarily influenced by carbon number). The second separation stage can then correspond to a GC separation based on another type of property, such as aromaticity or aromatic groups. As an example, consider two compounds with sufficiently distinct boiling points that the compounds exit the first GC separation stage at substantially different times, such as 20 seconds apart. The second GC separation stage preferably has a residence time that is sufficiently short so that the compound that exits the first GC separation stage at a substantially later time does not have an opportunity to "catch up" to the earlier compound during the second GC separation stage. Of course, such crossover of compounds may still occur in the second GC separation stage if the compounds exit the first GC separation stage at similar times. This is not a problem, as the benefit of the second GC separation stage is to provide an additional separation for those compounds that exit the first GC stage at similar times. Instead, the goal of having the second GC separation stage operate relatively quickly is to reduce or minimize situations where compounds that are clearly distinct based on the first GC separation stage become mixed or merged together again in the second GC separation stage.

In various embodiments, the second GC separation stage can have a characteristic residence time on the order of seconds. For example, the longest residence time for compounds that are passed into the second GC separation stage from the first GC separation stage can be about 20 seconds or less, such as about 15 seconds or less or about 10 seconds or less. So long as the second GC separation stage is effective for providing additional separation, the minimum residence time for a compound to exit the second GC separation stage is not critical. For example, minimum residence times for compounds exiting the second GC separation stage of can be at least 0.1 seconds, such as at least 0.25 seconds or at least 0.5 seconds. Optionally, the minimum residence time for the second GC separation stage can also be characterized based on compounds with at least a threshold molecular weight, such as compounds with a molecular weight of at least 60 Daltons, such as at least 80 Daltons or at least 100 Daltons.

For 2D-GC, a suitable system is an Agilent 6890 gas chromatograph (Agilent Technology, Wilmington, Del.) configured with a split/splitless inlet, capillary columns, and detector. The capillary column system contains a first-dimensional column, which is a BPX-5, 30 m, 0.25 mm i.d., 1.0 μm film, and a second-dimensional column, which is a BPX-50, 2 m, 0.25 mm i.d., 0.25 μm film. Both columns are manufactured by SGE Inc. (Austin, Tex.). There is a looped jet thermal modulation assembly (Zoex Corp., Lincoln, Nebr.) located in between the first and the second dimension columns. This modulator assembly contains a liquid nitrogen cooled "trap-release" jet thermal modulator with a looped transfer column.

Optionally a detection system can be used for the 2D-GC measurements described herein. The detection system can be, for example, a flame ionization detector. Flame ionization is useful method for quantitative detection of the amount of carbon in a sample. In a flame ionization detector, a sample is passed through a flame formed from combustion of hydrogen and either oxygen or compressed air. This pyrolyzes the sample and generates ions based on the compounds (such as hydrocarbons) in the sample. The flame ionization is performed between two electrodes which serve as detectors. The signal generated from flame ionization is proportional to the mass of the hydrocarbons in the sample, which make the detector suitable for quantitative characterization.

To provide characterization of a sample, the results from the 2D-GC are correlated with a MI. It has been surprisingly found that correlation of the amount of 2-8 ring aromatics, preferably 3-6 ring aromatics, more preferably 3.5-5.5 ring aromatics, in the hydrocarbon stream from the 2D-GC analysis with the MI is improved as compared to correlation of the amount of 2-8 ring aromatics, preferably 3-6 ring aromatics, more preferably 3.5-5.5 ring aromatics, in the hydrocarbon stream from UV aromatics or VI with the MI.

As used herein, the MI was determined in accordance with a Modified Ames Test. The Modified Ames Test was developed by Mobil Oil Corporation scientists as a screening assay for the dermal carcinogenicity of petroleum oils. The method has become the most widely used short-term biological assay in the petroleum industry. It was adopted in 1995 as ASTM Standard Method E 1687.

In developing the assay, the standard Ames mutagenicity assay was modified to provide maximum sensitivity to the class of compounds chiefly responsible for the mutagenicity and carcinogenicity of petroleum oils, i.e., polycyclic aromatic compounds. A series of oils already evaluated in mouse skin-painting bioassay was tested using the modified mutagenicity test, and their mutagenic responses quantified by regression analysis of the dose responses. The slopes resulting from these analyses, termed mutagenicity indices, or MIs, were then correlated with analogous carcinogenicity indices (CIs) calculated from the tumor responses seen in the skin-painting bioassays. The standard curve thus derived was used to establish an MI threshold above which an oil would be expected to demonstrate statistically significant carcinogenic activity in a skin-painting assay.

Since the correlation between MI and CI holds because both the mutagenicity and carcinogenicity of oils are mediated largely, if not exclusively, by polycyclic aromatic compounds, the Modified Ames Test's applicability is limited to test materials containing these compounds. This category includes petroleum refinery streams, as well as used or rerefined oils, coal-derived tars and oils, and formulated products comprised in part of such materials, provided there are no components present in the formulation that interfere with the performance or interpretation of the test.

The endpoint of the Modified Ames Test is the mutagenicity index or MI. It is the slope of the dose-response curve for mutagenicity, as determined using linear regression analysis. MIs can range from zero for highly refined oils to greater than 1,200 for certain catalytically cracked stocks.

Correlation of MI with dermal carcinogenic potential in the mouse skin-painting bioassay has shown that most oils with MIs greater than 1.0 are carcinogenic, while most with MIs less than 1.0 are not. The exception to the latter specification is the class of oils known as bright stock extracts or residual aromatic extracts which, to be certified non-carcinogenic in the European Union, must have MIs less than 0.4

In accordance with this disclosure, assessment of potential toxicological hazards of a hydrocarbon mixture can be made by measuring MI of processed base oils. The MI threshold value for such an assessment is preferably 0.4. Base oils for which the MI is greater than 0.4 are considered to be samples for which potential health hazards should be more fully quantified. 2D-GC quantification of 2-8 ring aromatics, preferably 3-6 ring aromatics, more preferably 3.5-5.5 ring aromatics, exhibits a stronger relationship with MI than other quick methods to quantify the level of multi-ring aromatics in samples, such as UV aromatics and VI. Evaluation with 2D-GC of a diverse set of samples (i.e., crude, distillate, raffinate, extract, and dewaxed oil) originating from various feeds showed the 3.5-5.5 aromatic ring class region of 2D-GC spectra were present in samples with MI greater than 0.4, yet greatly diminished from samples with MI less than 0.4. The 2D-GC analysis can quantify multi-ring aromatics in a similar fashion to HDHA and the 2D-GC method is faster and less expensive.

In accordance with this disclosure, the robustness or strength of the relationship between MI and the weight percentage of 2-8 ring aromatic molecules, preferably 3-6 ring aromatic molecules, more preferably 3.5-5.5 ring aromatic molecules, identified by completing 2D-GC analysis in the hydrocarbon stream is greater or improved as compared to the robustness or strength of the relationship between MI and the weight percentage of 2-8 ring aromatic molecules, preferably 3-6 ring aromatic molecules, more preferably 3.5-5.5 ring aromatic molecules, identified by completing UV aromatics or VI analysis in the hydrocarbon stream.

Also, with this range of aromatics, there is a strong and surprising preference for the aromatics boiling within the 700 to 800 deg F. range. While it might be expected that more complex aromatic molecules present greater tendency for increased MI, it is this boiling range that appears to have the greatest impact on the MI result.

Also, in accordance with this disclosure, a MI threshold value above 0.4 is indicative of the presence of 2-8 ring aromatics, preferably 3-6 ring aromatics, more preferably 3.5-5.5 ring aromatics, in the hydrocarbon stream, and thereby is indicative of a potential toxicological hazard. A MI threshold value below 0.4 is indicative of the absence of 2-8 ring aromatics, preferably 3-6 ring aromatics, more preferably 3.5-5.5 ring aromatics, in the hydrocarbon stream, and thereby is indicative of no potential toxicological hazard.

Further, in accordance with this disclosure, the hydrocarbon stream is used for base stock production. In an embodiment, the hydrocarbon stream is selected from a crude, a distillate, a raffinate, an extract, a dewaxed oil, and the like. Illustrative hydrocarbon streams include, for example, a whole crude, total liquid product (TLP) from a process unit, a total liquid product from a research or refinery process, a fraction, distillate or intermediate stream of whole crude, TLP or intermediate, or a fraction, distillate or intermediate stream from research or refinery process.

The method of this disclosure enables a lube refinery to more effectively capture feed flexibility credits and reduce product give away during Group I/II/III/III+ base stock production.

2D-GC is a faster and less expensive method to identify multi-ring aromatics than more detailed techniques, and 2D-GC can identify a broader range of aromatic classes than other quick methods. It has the potential to be field deployable, providing real time feedback during commercial feed selection and stock switching at refineries.

This composition of this disclosure comprises a middle distillate boiling range refined petroleum stream having a 4.5 ring value of less than about 70 wppm, a final boiling point (FBP) of less than about 1100° F., and a MI of 1. In particular, the composition has a kinematic viscosity at 100° C. between about 4 and about 12 cSt, and a viscosity index (VI) of at least 75. Preferably, the distillate is a refined lube base stock suitable for formulation in lubricants.

The following non-limiting examples are provided to illustrate the disclosure.

EXAMPLES

Experimental Summary

A laboratory study was performed where various petroleum based oils were analyzed with 2D-GC, toxic potential was quantified via measurements of Modified-Ames Mutagenicity Index (MI) and model estimations of Modified-Ames Mutagenicity Index. Additionally, VI and UV aromatics of the base oils were measured. Data was used to better understand required processing severity needed to reduce MI below 0.4, and evaluate use of 2D-GC as a MI screening tool in comparison to model estimations, UV aromatics and VI data. MI was less than 0.4 for the oils extracted at low and mild severity. Quantitative analysis of oils showed 2D-GC, 3.5-5.5 aromatic ring class distribution can be used to evaluate the MI of the MIDW samples and was surprisingly a better indicator than UV absorbance and VI measurements. Additionally, a more diverse set of samples (e.g., crude, distillate, raffinate, extract, dewaxed oil, and the like) originating from various feeds, generated from lubes assay work, were submitted for MI and analyzed with 2D-GC. The MI of these samples was also correctly gauged using 2D-GC quantification of aromatics distribution.

Example 1

Figure 1:
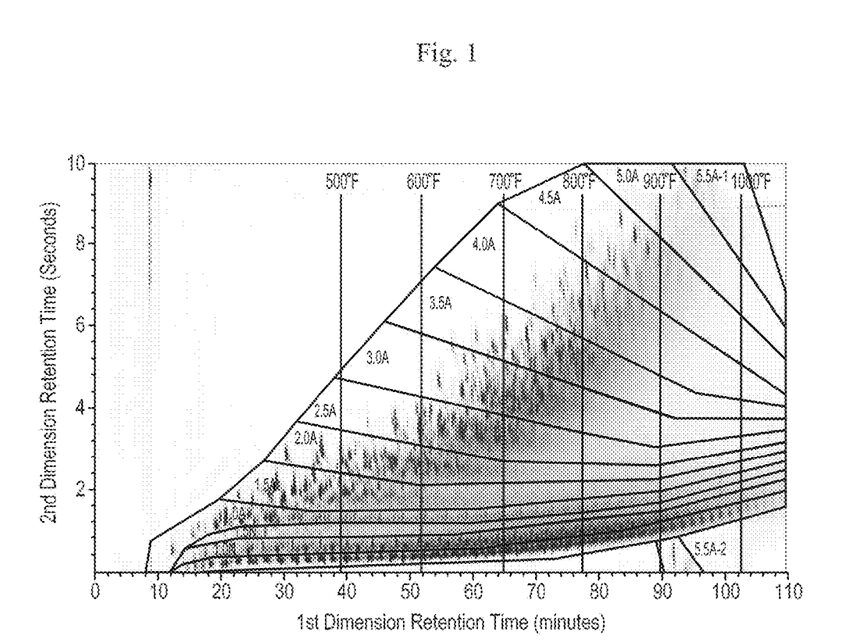
FIG. 1 shows 2D-GC spectra of distillate and base oils in accordance with Example 1.
Figure 2:
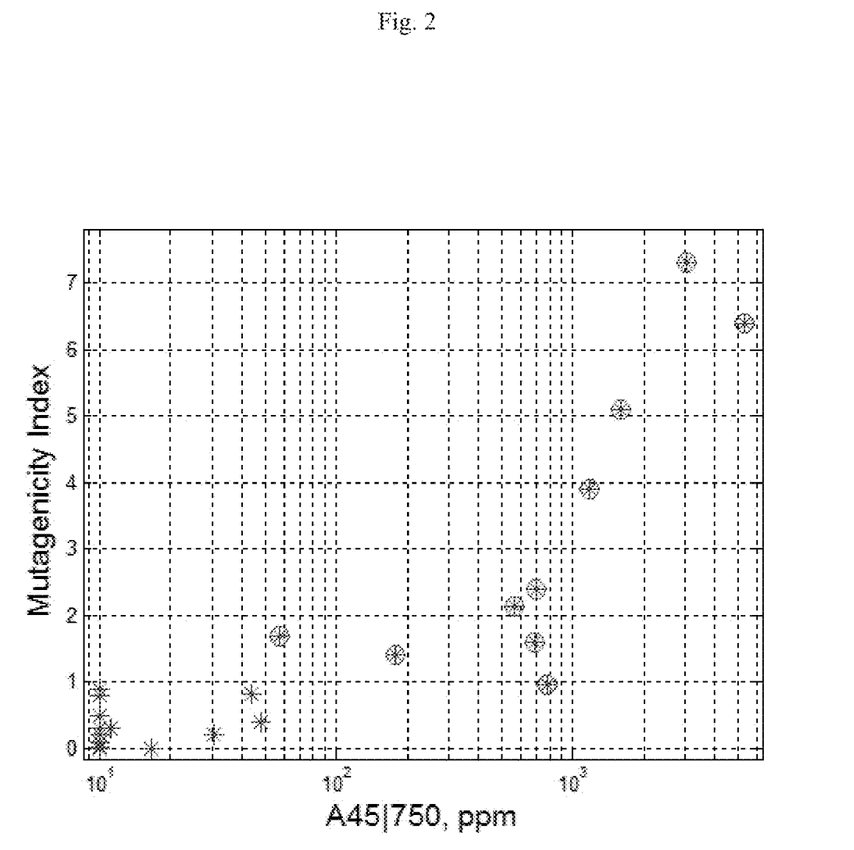
FIG. 2 depicts a plot showing MI versus the 4.5 ring aromatics by 2DGC, in wppm over a broad range of petroleum fractions plot showing the relationship of MI with the 2DGC analysis for 4.5 aromatic rings boiling between 700 and 800 deg F.
Figure 3:
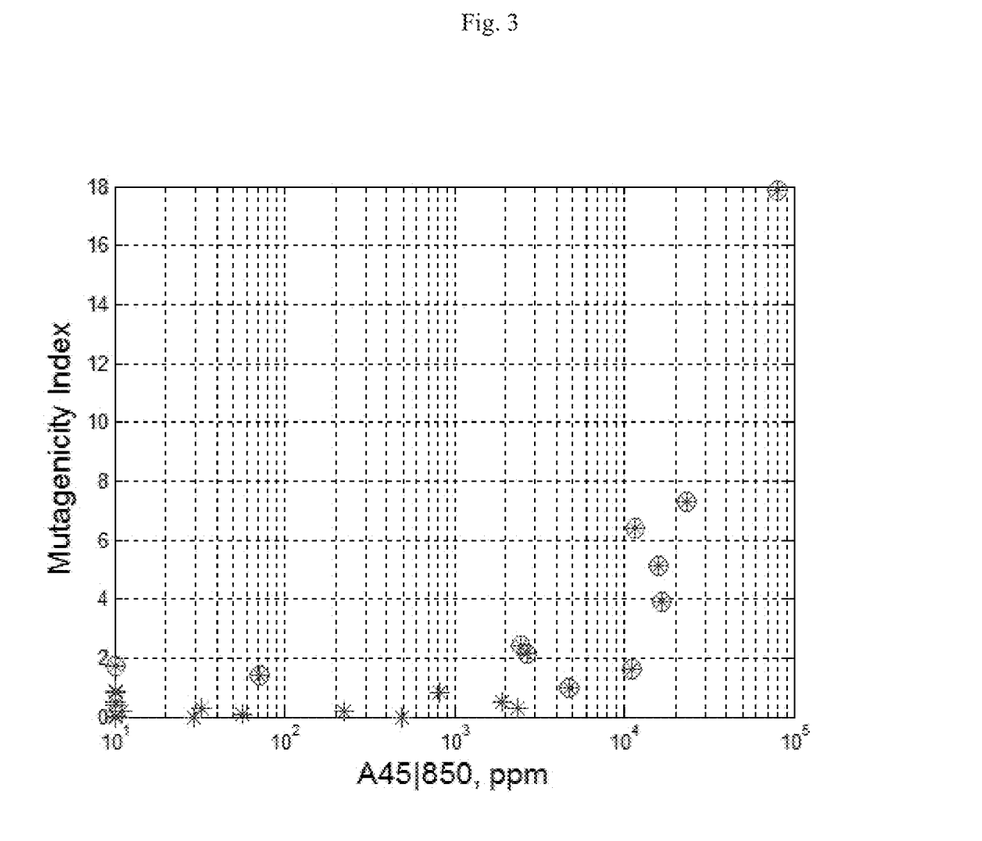
FIG. 3 depicts a plot showing MI versus the 4.5 ring aromatics by 2DGC, in wppm over a broad range of petroleum fractions plot showing the relationship of MI with the 2DGC analysis for 4.5 aromatic rings boiling between 800 and 900 deg F.
Figure 4:
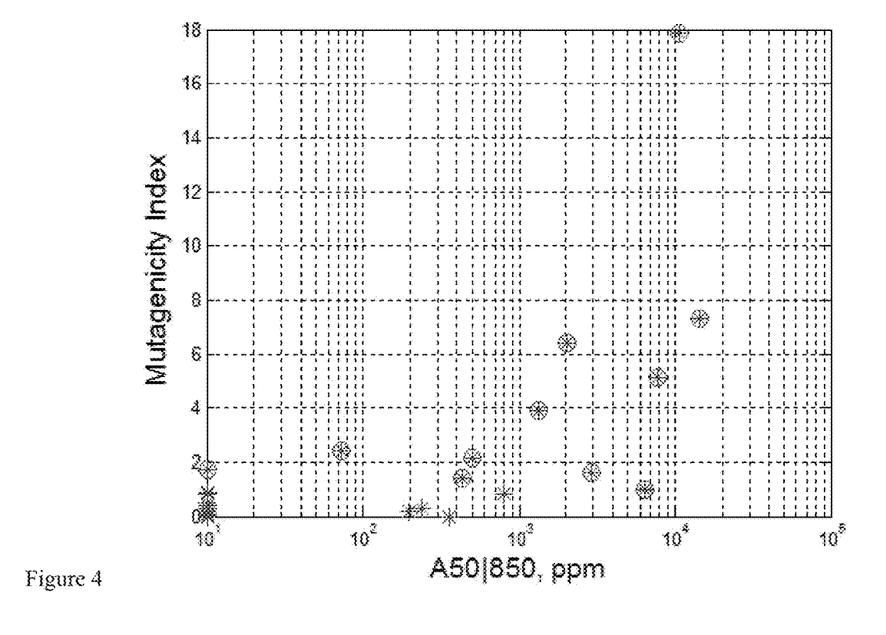
FIG. 4 depicts a plot showing MI versus the 5 ring aromatics by 2DGC, in wppm over a broad range of petroleum fractions plot showing the relationship of MI with the 2DGC analysis for 4.5 aromatic rings boiling between 800 and 900 deg F.
Figure 5:
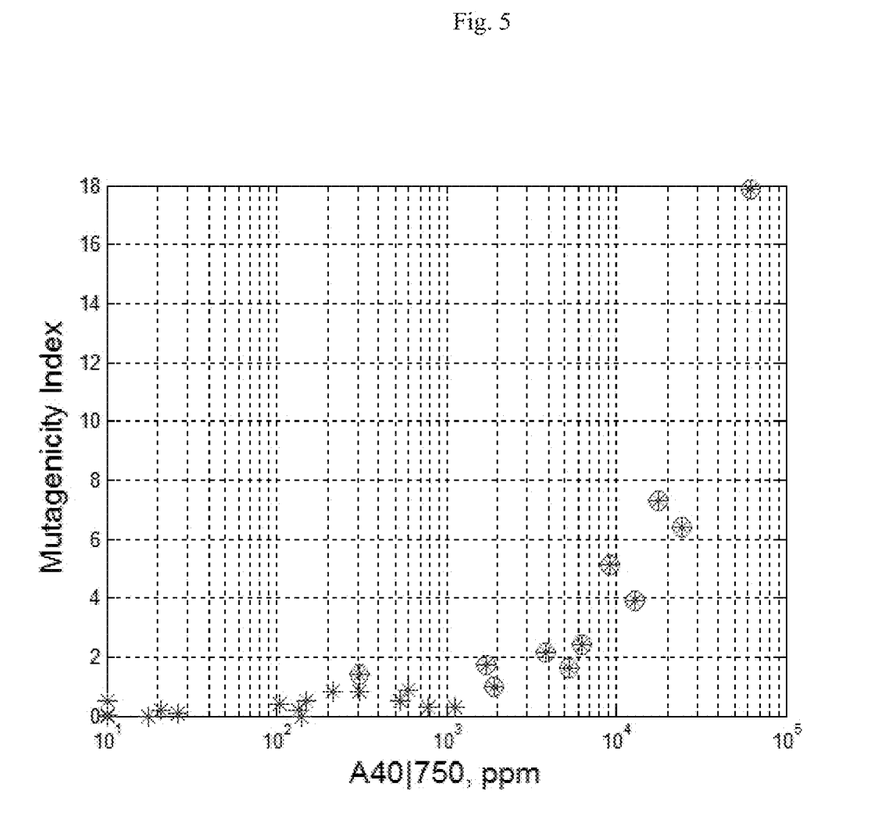
FIG. 5 depicts a plot showing MI versus the 4 ring aromatics by 2DGC, in wppm over a broad range of petroleum fractions plot showing the relationship of MI with the 2DGC analysis for 4 aromatic rings boiling between 700 and 800 deg F.
Figure 7:
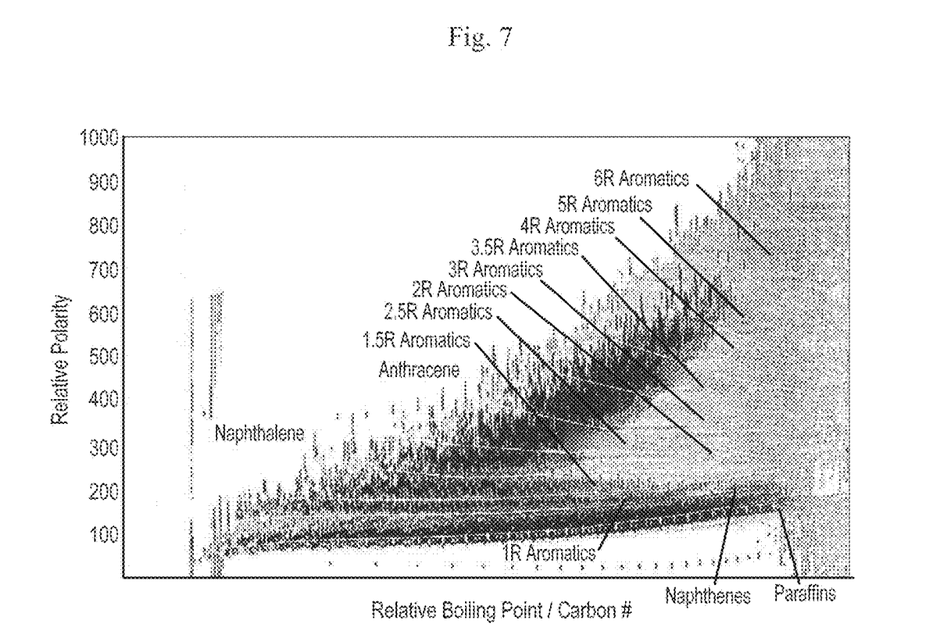
FIG. 7 is a rendition of the 2D-GC chromatogram indicating general ring class areas.

2D-GC spectra of a variety of distillates and base oils from were analyzed by 2DGC. Individual results for both ring class and boiling range were compiled and correlated. While higher aromatics in general were often believed to be associated with higher MI, surprisingly, the single parameter of 4.5 rings boiling between 700 and 8800 deg C. persuasively predicted the resulting MI of the entire sample. This was quite unexpected since there are a range of aromatics compounds across the boiling ranges, but a composition of less than 70 wppm by this method was sufficient in separating entire samples whose MI was less than 1.0. (FIG. 2) Other categories of ring compounds also showed similar general trends, but not to the degree of FIG. 2. As an example, FIG. 3 examines the same ring class but at 100 deg F. higher boiling range and it does not distinguish the MI of the samples above and below 1. It is similar for other parameters as seen in FIGS. 4 and 5. These other related parameters could be included in a multi-parameter approach is need with the appropriate plots generated.

Example 2

Figure 8:
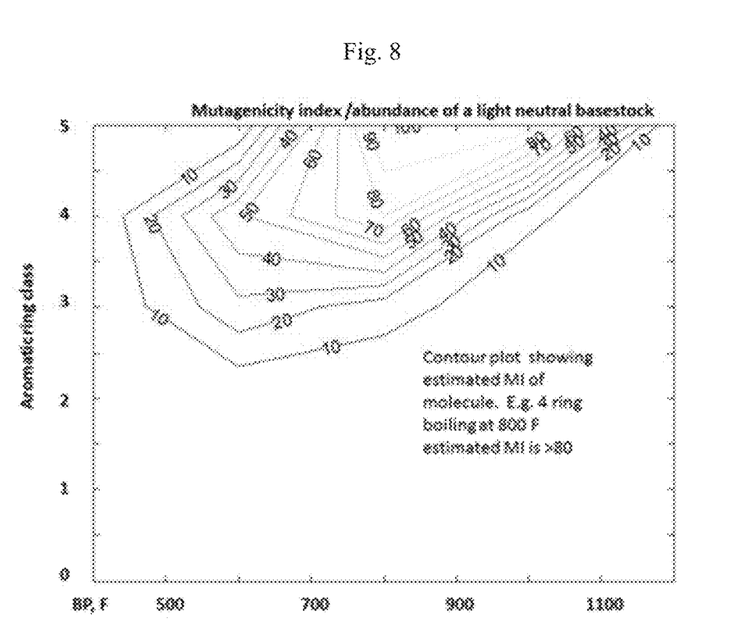
FIG. 8 is a contour plot showing estimated MI for a typical molecule from modeling for LN base stock
Figure 9:
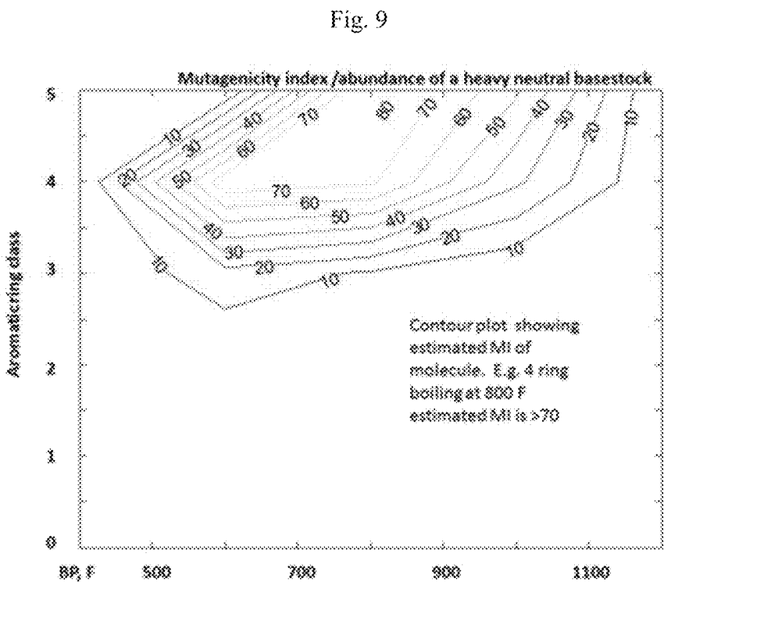
FIG. 9 is a contour plot showing estimated MI from for a typical molecule from modeling for HN base stock.
Figure 10:
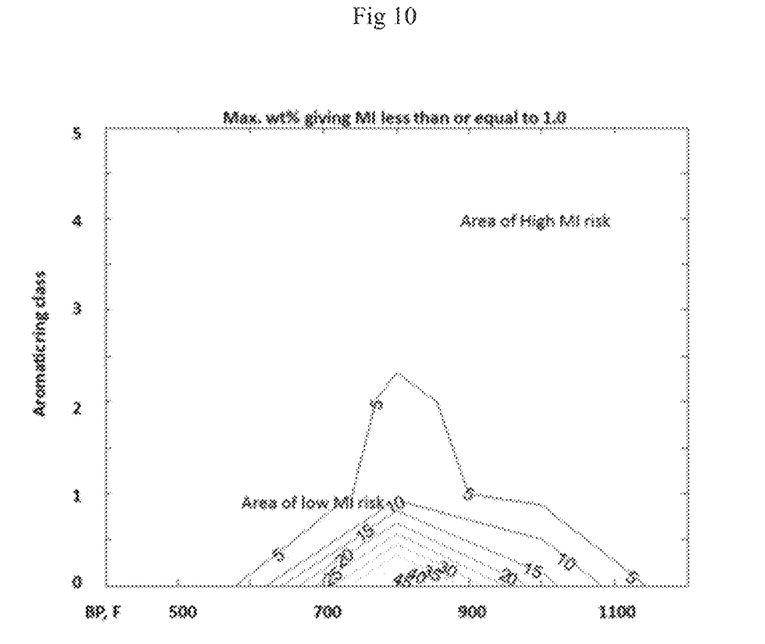
FIG. 10 indicates modeling contours for oils with significant amounts (>5%) of components that have MI<1 occur only for saturates and lower ring class molecules (<2 aromatics rings).
Figure 11:
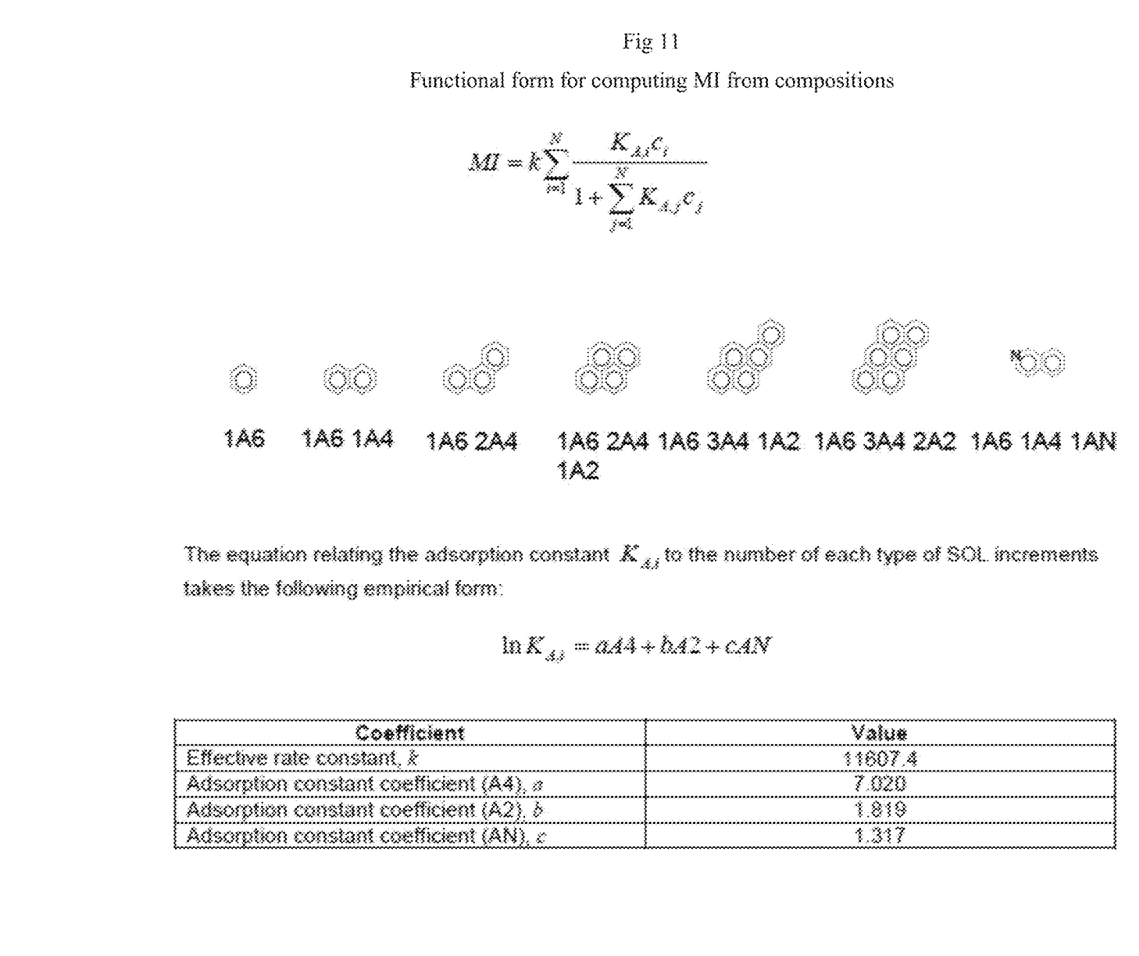
FIG. 11 shows the functional form used in the model along with modeled cores, ring classes and regression coefficients.

An alternate analytical and modeling technique, HDHA was conducted on a set of oils that spanned MI values form 0 to above 10. The general outline of the analytical scheme is detailed in U.S. Pat. No. 8,682,597, herein incorporated by reference in its entirety. An absorption model was developed and found to model the results well and was capable of predicting the individual MI's of the various ring classes. Surprisingly, only three significant variables were found from this exercise, specifically the A4, the A2 and the nitrogen-containing AN (see FIG. 11 for full details). Using the regressed coefficients, the MI for the pure ring class variable may be estimated (see FIGS. 8 and 9). In order to keep an entire sample less than an MI of 1, less than 0.1% and most preferably less than 0.01% of the final stock would need to be within these higher ring classes. Of particular note, the Aromatics rings of about 4.5 and around 800 deg. F. are the most constraining for both viscosity grades.

PCT and EP Clauses:

1. A method of screening a hydrocarbon stream for potential toxicological hazards, said method comprising:
   providing a hydrocarbon stream;
   conducting 2-dimensional gas chromatography (2D-GC) analysis to quantify saturates and aromatic distribution in the hydrocarbon stream;
   identifying 2-8 ring aromatic distribution and weight percentage of 2-8 ring aromatic molecules in the hydrocarbon stream from the 2D-GC analysis; wherein the 2-8 ring aromatic distribution comprises mono alkylated aromatic molecules and multi alkylated aromatic molecules;
   relating the weight percentage of 2-8 ring aromatic molecules in the hydrocarbon stream from the 2D-GC analysis to a mutagenicity index (MI), wherein the MI is determined in accordance with ASTM Standard Method E 1687; and
   assessing a potential toxicological hazard of the hydrocarbon stream based on the weight percentage of 2-8 ring aromatic molecules in the hydrocarbon stream from the 2D-GC analysis and a MI threshold value.

2. The method of clause 1 wherein the hydrocarbon stream is selected from the group consisting of a crude, a distillate, a raffinate, an extract, and a dewaxed oil.

3. The method of clause 1 wherein the hydrocarbon stream comprises a whole crude, total liquid product (TLP) from a process unit, a total liquid product from a research or refinery process, a fraction, distillate or intermediate stream of whole crude, TLP or intermediate, or a fraction, distillate or intermediate stream from a research or refinery process.

4. The method of clauses 1-3 wherein the MI threshold value is 0.4.

5. The method of clauses 1-4 wherein the robustness or strength of the relationship between MI and the weight percentage of 2-8 ring aromatic molecules identified by completing 2D-GC analysis in the hydrocarbon stream is greater or improved as compared to the robustness or strength of the relationship between MI and the weight percentage of 2-8 ring aromatic molecules identified by completing UV aromatics or VI analysis in the hydrocarbon stream.

6. The method of clauses 1-5 wherein a MI threshold value above 0.4 is indicative of (i) the presence of 2-8 ring aromatics in the hydrocarbon stream, and (ii) a potential toxicological hazard.

7. The method of clauses 1-6 wherein the 2-8 ring aromatics comprise 3-6 ring aromatics or 3.5-5.5 ring aromatics.

8. A method of characterizing a hydrocarbon stream, said method comprising:
   providing a hydrocarbon stream;
   conducting 2-dimensional gas chromatography (2D-GC) analysis to quantify saturates and aromatic distribution in the hydrocarbon stream;
   identifying 2-8 ring aromatic distribution and weight percentage of 2-8 ring aromatic molecules in the hydrocarbon stream from the 2D-GC analysis; wherein the 2-8 ring aromatic distribution comprises mono alkylated aromatic molecules and multi alkylated aromatic molecules; and
   relating the weight percentage of 2-8 ring aromatic molecules in the hydrocarbon stream from the 2D-GC analysis with a mutagenicity index (MI), wherein the MI is determined in accordance with ASTM Standard Method E 1687.

9. The method of clause 8 further comprising:
   assessing a potential toxicological hazard of the hydrocarbon stream based on the weight percentage of 2-8 ring aromatic molecules in the hydrocarbon stream from the 2D-GC analysis and a MI threshold value.

10. The method of clause 8 wherein the hydrocarbon stream is selected from the group consisting of a crude, a distillate, a raffinate, an extract, and a dewaxed oil.

11. The method of clause 8 wherein the hydrocarbon stream comprises a whole crude, total liquid product (TLP) from a process unit, a total liquid product from a research or refinery process, a fraction, distillate or intermediate stream of whole crude, TLP or intermediate, or a fraction, distillate or intermediate stream from a research or refinery process.

12. The method of clauses 8-11 wherein the MI threshold value is 0.4.

13. The method of clauses 8-12 wherein the robustness or strength of the relationship between MI and the weight percentage of 2-8 ring aromatic molecules identified by completing 2D-GC analysis in the hydrocarbon stream is greater or improved as compared to the robustness or strength of the relationship between MI and the weight percentage of 2-8 ring aromatic molecules identified by completing UV aromatics or VI analysis in the hydrocarbon stream.

14. The method of clauses 8-13 wherein a MI threshold value above 0.4 is indicative of (i) the presence of 2-8 ring aromatics in the hydrocarbon stream, and (ii) a potential toxicological hazard.

15. A composition comprising a middle distillate boiling range refined petroleum stream having a 4.5 ring value of less than 70 wppm, a final boiling point (FBP) of less than 1100° F., and a MI of less than 1.

16. A composition comprising a middle distillate or lube range material with a stream 4.5 ring value of less than about 0.1 and a MI of less than 1.

17. A composition comprising a middle distillate boiling range refined petroleum stream having a ring class parameter between 3.5 and 5.5 aromatic rings, boiling between 700 and 900 deg. F. and an MI of less than 1, and wherein the 4.5 ring value is less than 100 wppm.

All patents and patent applications, test procedures (such as ASTM methods, UL methods, and the like), and other documents cited herein are fully incorporated by reference to the extent such disclosure is not inconsistent with this disclosure and for all jurisdictions in which such incorporation is permitted.

When numerical lower limits and numerical upper limits are listed herein, ranges from any lower limit to any upper limit are contemplated. While the illustrative embodiments of the disclosure have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside in the present disclosure, including all features which would be treated as equivalents thereof by those skilled in the art to which the disclosure pertains.

The present disclosure has been described above with reference to numerous embodiments and specific examples. Many variations will suggest themselves to those skilled in this art in light of the above detailed description. All such obvious variations are within the full intended scope of the appended claims.

The invention claimed is:

1. A method of screening a hydrocarbon stream for potential toxicological hazards, said method comprising:
    providing a hydrocarbon stream;
    conducting 2-dimensional gas chromatography (2D-GC) analysis to quantify saturates and aromatic distribution in the hydrocarbon stream;
    identifying 2-8 ring aromatic distribution and weight percentage of 2-8 ring aromatic molecules in the hydrocarbon stream from the 2D-GC analysis, wherein the 2-8 ring aromatic distribution comprises mono alkylated aromatic molecules and multi alkylated aromatic molecules;
    relating the weight percentage of 2-8 ring aromatic molecules in the hydrocarbon stream from the 2D-GC analysis to a mutagenicity index (MI), wherein the MI is determined in accordance with ASTM Standard Method E 1687; and
    assessing a potential toxicological hazard of the hydrocarbon stream based on the weight percentage of 2-8 ring aromatic molecules in the hydrocarbon stream from the 2D-GC analysis and a MI threshold value.

2. The method of claim 1 wherein the hydrocarbon stream is used for base stock production.

3. The method of claim 1 wherein the hydrocarbon stream is selected from the group consisting of a crude, a distillate, a raffinate, an extract, and a dewaxed oil.

4. The method of claim 1 wherein the hydrocarbon stream comprises a whole crude, total liquid product (TLP) from a process unit, a total liquid product from a research or refinery process, a fraction, distillate or intermediate stream of whole crude, TLP or intermediate, or a fraction, distillate or intermediate stream from a research or refinery process.

5. The method of claim 1 wherein the MI threshold value is 0.4.

6. The method of claim 1 wherein a robustness or strength of the relationship between MI and the weight percentage of 2-8 ring aromatic molecules identified by completing 2D-GC analysis in the hydrocarbon stream is greater or improved as compared to a robustness or strength of the relationship between MI and the weight percentage of 2-8 ring aromatic molecules identified by completing UV analysis or VI analysis in the hydrocarbon stream.

7. The method of claim 1 wherein a MI threshold value above 0.4 is indicative of a presence of 2-8 ring aromatic molecules in the hydrocarbon stream.

8. The method of claim 1 wherein a MI threshold value above 0.4 is indicative of a potential toxicological hazard.

9. The method of claim 1 wherein a MI threshold value below 0.4 is indicative of an absence of 2-8 ring aromatic molecules in the hydrocarbon stream.

10. The method of claim 1 wherein a MI threshold value below 0.4 is indicative of no potential toxicological hazard.

11. The method of claim 1 wherein the 2-8 ring aromatic molecules comprise 3-6 ring aromatics or 3.5-5.5 ring aromatics.

12. The method of claim 1 wherein the MI is determined by a Modified Ames Test in accordance with ASTM Standard Method E 1687 10.

13. A method of characterizing a hydrocarbon stream, said method comprising:
    providing a hydrocarbon stream;
    conducting 2-dimensional gas chromatography (2D-GC) analysis to quantify saturates and aromatic distribution in the hydrocarbon stream;
    identifying 2-8 ring aromatic distribution and weight percentage of 2-8 ring aromatic molecules in the hydrocarbon stream from the 2D-GC analysis wherein the 2-8 ring aromatic distribution comprises mono alkylated aromatic molecules and multi alkylated aromatic molecules; and
    relating the weight percentage of 2-8 ring aromatic molecules in the hydrocarbon stream from the 2D-GC analysis with a mutagenicity index (MI), wherein the MI is determined in accordance with ASTM Standard Method E 1687.

14. The method of claim 13 further comprising:
    assessing a potential toxicological hazard of the hydrocarbon stream based on the weight percentage of 2-8 ring aromatic molecules in the hydrocarbon stream from the 2D-GC analysis and a MI threshold value.

15. The method of claim 13 wherein the hydrocarbon stream is used for base stock production.

16. The method of claim 13 wherein the hydrocarbon stream is selected from the group consisting of a crude, a distillate, a raffinate, an extract, and a dewaxed oil.

17. The method of claim 13 wherein the hydrocarbon stream comprises a whole crude, tempered liquefied petroleum gas (TLP) from a process unit, a total liquid product from a research or refinery process, a fraction, distillate or intermediate stream of whole crude, TLP or intermediate, or a fraction, distillate or intermediate stream from a research or refinery process.

18. The method of claim 14 wherein the MI threshold value is 0.4.

19. The method of claim 13 wherein a robustness or strength of the relationship between MI and the weight percentage of 2-8 ring aromatic molecules identified by completing 2D-GC analysis in the hydrocarbon stream is greater or improved as compared to a robustness or strength of the relationship between MI and the weight percentage of 2-8 ring aromatic molecules identified by completing UV analysis or VI analysis in the hydrocarbon stream.

20. The method of claim 14 wherein a MI threshold value above 0.4 is indicative of a presence of 2-8 ring aromatic molecules in the hydrocarbon stream.

21. The method of claim 13 wherein a MI threshold value above 0.4 is indicative of a potential toxicological hazard.

22. The method of claim 14 wherein a MI threshold value below 0.4 is indicative of an absence of 2-8 ring aromatic molecules in the hydrocarbon stream.

23. The method of claim 14 wherein a MI threshold value below 0.4 is indicative of no potential toxicological hazard.

24. The method of claim 13 wherein the 2-8 ring aromatic molecules comprise 3-6 ring aromatic molecules or 3.5-5.5 ring aromatic molecules.

25. The method of claim 13 wherein the MI is determined by a Modified Ames Test in accordance with ASTM Standard Method E 1687 10.

26. A method of screening a hydrocarbon stream for potential toxicological hazards, said method comprising:
provide a hydrocarbon stream;
conducting high detail hydrocarbon analysis (HDHA) to quantify saturates, heteroatom and aromatic distribution in the hydrocarbon stream;
identifying a 2-8 ring aromatic distribution and weight percentage of 2-8 ring aromatic molecules in the hydrocarbon stream from the HDHA analysis, wherein the 2-8 ring aromatic distribution comprises mono alkylated aromatic molecules and multi alkylated aromatic molecules;
relating the weight percentage of 2-8 ring aromatic molecules in the hydrocarbon stream from the HDHA analysis to a mutagenicity index (MI), wherein the MI is determined in accordance with ASTM Standard Method E 1687; and
assessing a potential toxicological hazard of the hydrocarbon stream based on the weight percentage of 2-8 ring aromatic molecules in the hydrocarbon stream from the HDHA analysis and a MI threshold value.

27. A composition comprising a middle distillate boiling range refined petroleum stream having a 4.5 ring value of less than about 70 ppm, a final boiling point (FBP) of less than about 1100° F., and a MI of 1.

28. The composition of claim 27 having a kinematic viscosity at 100° C. between about 4 and about 12 cSt.

29. The composition of claim 27 having a viscosity index (VI) of at least 75.

30. The composition of claim 27 wherein the middle distillate boiling range refined petroleum stream is a refined lube base stock suitable for formulation in lubricants.

31. A composition comprising a middle distillate boiling range refined petroleum stream having an HDHA ring class value of 4+ ring boiling of about 800 deg. F., a ring value of less than about 0.01% ppm, a final boiling point (FBP) of less than about 1100° F., and a MI of 1.

* * * * *